United States Patent
Feng et al.

(10) Patent No.: US 6,998,424 B2
(45) Date of Patent: Feb. 14, 2006

(54) CLEAR SILICONE MICROEMULSIONS FORMED SPONTANEOUSLY

(75) Inventors: Qian Jane Feng, Midland, MI (US); Zuchen Lin, Midland, MI (US); Randal Myron Hill, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 67 days.

(21) Appl. No.: 10/683,490

(22) Filed: Oct. 10, 2003

(65) Prior Publication Data

US 2004/0077776 A1 Apr. 22, 2004

Related U.S. Application Data

(63) Continuation-in-part of application No. 09/917,322, filed on Jul. 30, 2001, now abandoned.

(51) Int. Cl.
*B01F 3/08* (2006.01)
*B01F 17/54* (2006.01)

(52) U.S. Cl. .................. 516/53; 516/55; 525/477; 524/266; 524/268

(58) Field of Classification Search .............. 524/837; 525/477; 516/53, 55
See application file for complete search history.

(56) References Cited

U.S. PATENT DOCUMENTS

| | | | |
|---|---|---|---|
| 4,311,695 A | 1/1982 | Starch | 424/184 |
| 4,675,179 A | 6/1987 | Suzuki et al. | 424/67 |
| 4,782,095 A | 11/1988 | Gum | 514/937 |
| 4,980,156 A | 12/1990 | Raleigh et al. | 424/66 |
| 5,008,103 A | 4/1991 | Raleigh et al. | 424/66 |
| 5,451,692 A | 9/1995 | Raleigh et al. | 556/445 |
| 5,606,613 A | 2/1997 | Lee et al. | 424/78.03 |
| 5,705,562 A | 1/1998 | Hill | 524/731 |
| 6,071,975 A | 6/2000 | Halloran | 516/58 |
| 6,632,420 B1 * | 10/2003 | Cen et al. | 424/65 |
| 2002/0143072 A1 * | 10/2002 | Aust | 516/98 |

FOREIGN PATENT DOCUMENTS

| | | |
|---|---|---|
| EP | 0 995 771 A2 | 4/2000 |
| EP | WO 02/26204 A2 | 4/2002 |

* cited by examiner

*Primary Examiner*—Marc Zimmer
(74) *Attorney, Agent, or Firm*—Jim L. De Cesare; Alan Zombeck

(57) ABSTRACT

Clear microemulsions are formed spontaneously by combining (i) water; (ii) a volatile siloxane; (iii) a long chain or high molecular weight silicone polyether; and, as an optional ingredient, (iv) a cosurfactant such as a monohydroxy alcohol, an organic diol, an organic triol, an organic tetraol, a silicone diol, a silicone triol, a silicone tetraol, and a nonionic organic surfactant. In an alternate embodiment, a non-volatile siloxane is included as an ingredient, and the silicone polyether is a long chain or high molecular weight silicone polyether, or a short chain or low molecular weight silicone polyether.

5 Claims, No Drawings

CLEAR SILICONE MICROEMULSIONS FORMED SPONTANEOUSLY

CROSS-REFERENCE TO RELATED APPLICATIONS

This application is a continuation in part of U.S. application Ser. No. 09/917,322, filed on Jul. 30, 2001, now abandoned.

FIELD OF THE INVENTION

This invention is related to clear silicone microemulsions that form spontaneously without input of significant mechanical energy, and more particularly to the use of certain longer chain, higher molecular weight species of silicone polyether (SPE) as primary surfactant. They can also be used in forming clear silicone microemulsions containing oil phases consisting of mixtures of volatile as well as nonvolatile silicone oils.

BACKGROUND OF THE INVENTION

Microemulsions are clear or transparent because they contain particles smaller than the wavelength of visible light, i.e., typically 10–100 nanometer. They can contain oil droplets dispersed in water (O/W), water droplets dispersed in oil (W/O), or they may be bi-continuous in their structure. They are characterized by ultra low interfacial tension between oil and water phases.

While U.S. Pat. No. 5,705,562 (Jan. 6, 1998) teach the use of short chain or low molecular weight silicone polyethers in preparation of spontaneously formed clear silicone microemulsions, they do not teach preparing clear silicone microemulsions using long chain or high molecular weight silicone polyethers. This is not surprising as prior to this invention, there is nothing in the public domain relative to the preparation of clear silicone microemulsions using long chain or high molecular weight silicone polyethers.

The '562 patent, unlike the present invention, also fails to teach preparation of clear microemulsions from mixtures of both a volatile silicone oil and a nonvolatile silicone oil. Rather, the clear silicone microemulsions in the '562 patent are limited to oil phases containing only silicone oils which are volatile.

As a third distinction, according to the '562 patent, the composition should be free of non-essential ingredients such as cosurfactants. According to this invention, however, the composition may contain such non-essential cosurfactants, yet result in formation of clear silicone microemulsions.

BRIEF SUMMARY OF THE INVENTION

The invention relates clear microemulsions formed by simply combining as ingredients (i) water; (ii) a volatile siloxane; (iii) a long chain or high molecular weight silicone polyether; and, as an optional ingredient, (iv) a cosurfactant such as a monohydroxy alcohol, an organic diol, an organic triol, an organic tetraol, a silicone diol, a silicone triol, a silicone tetraol, and a nonionic organic surfactant.

In a second embodiment, the invention relates to clear microemulsions formed by simply combining as ingredients (i) water; (ii) a volatile siloxane; (iii) a non-volatile siloxane; (iv) a silicone polyether; and, as an optional ingredient, (v) a cosurfactant such as a monohydroxy alcohol, an organic diol, an organic triol, an organic tetraol, a silicone diol, a silicone triol, a silicone tetraol, and a nonionic organic surfactant.

A long chain or high molecular weight silicone polyether, or a short chain or low molecular weight silicone polyether can be used in this second embodiment.

For purposes of this invention, a clear microemulsions is a thermodynamically stable isotropic dispersion of oil (siloxane phase) and water having an average particle size of less than 100 nanometers. The clarity of these microemulsions are such that a 8 font size text can be read through a 1 cm layer sample of the composition.

These and other features of the invention will become apparent from a consideration of the detailed description.

DETAILED DESCRIPTION OF THE INVENTION

In a first embodiment of the invention, clear microemulsions are formed by simply combining the components (i) water; (ii) a volatile siloxane; (iii) a long chain or high molecular weight silicone polyether; and, as an optional component, (iv) a cosurfactant such as a monohydroxy alcohol, an organic diol, organic triol, organic tetraol, silicone diol, silicone triol, silicone tetraol, or nonionic organic surfactant.

The volatile siloxane used in this embodiment can be either volatile linear or cyclic methyl siloxanes. The volatile linear methyl siloxanes have the formula $(CH_3)_3SiO\{(CH_3)_2SiO\}_kSi(CH_3)_3$. The value of k is 0–5. The volatile cyclic methyl siloxanes have the formula $\{(CH_3)_2SiO\}_t$. The value of t is 3–9. Preferably, these volatile polydimethylsiloxanes have a boiling point less than about 250° C. and viscosity of about 0.65 to about 5.0 mm$^2$/s.

Some representative volatile linear methyl siloxanes are hexamethyldisiloxane (MM) with a boiling point of 100° C., viscosity of 0.65 mm$^2$/s, and formula $Me_3SiOSiMe_3$; octamethyltrisiloxane (MDM) with a boiling point of 152° C., viscosity of 1.04 mm$^2$/s, and formula $Me_3SiOMe_2SiOSiMe_3$; decamethyltetrasiloxane (MD$_2$M) with a boiling point of 194° C., viscosity of 1.53 mm$^2$/s, and formula $Me_3SiO(Me_2SiO)_2SiMe_3$; dodecamethylpentasiloxane (MD$_3$M) with a boiling point of 229° C., viscosity of 2.06 mm$^2$/s, and formula $Me_3SiO(Me_2SiO)_3SiMe_3$; tetradecamethylhexasiloxane (MD$_4$M) with a boiling point of 245° C., viscosity of 2.63 mm$^2$/s, and formula $Me_3SiO(Me_2SiO)_4SiMe_3$; and hexadecamethylheptasiloxane (MD$_5$M) with a boiling point of 270° C., viscosity of 3.24 mm$^2$/s, and formula $Me_3SiO(Me_2SiO)_5SiMe_3$.

Some representative volatile cyclic methyl siloxanes are hexamethylcyclotrisiloxane (D$_3$) a solid with a boiling point of 134° C. and formula $\{(Me_2)SiO\}_3$; octamethylcyclotetrasiloxane (D$_4$) with a boiling point of 176° C., viscosity of 2.3 mm$^2$/s, and formula $\{(Me_2)SiO\}_4$; decamethylcyclopentasiloxane (D$_5$) with a boiling point of 210° C., viscosity of 3.87 mm$^2$/s, and formula $\{(Me_2)SiO\}_5$; and dodecamethylcyclohexasiloxane (D$_6$) with a boiling point of 245° C., viscosity of 6.62 mm$^2$/s, and formula $\{(Me_2)SiO\}_6$.

The long chain or high molecular weight silicone polyether can have a structure represented by:

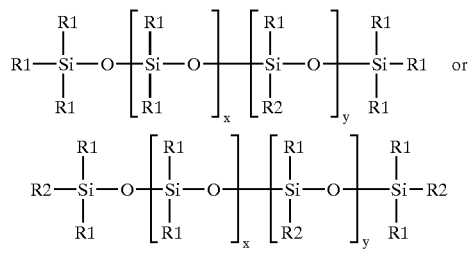

A cyclic polyether of the type shown below can also be used.

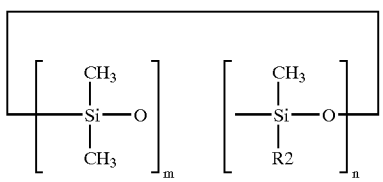

In these structures, R1 represents an alkyl group containing 1–6 carbon atoms such as methyl, ethyl, propyl, butyl, pentyl, and hexyl; R2 represents the radical—$(CH_2)_aO(C_2H_4O)_b(C_3H_6O)_cR3$; x has a value of 20–1,000, alternatively 20–200, or alternatively 20–50; y has a value of 2–500, alternatively 2–50, or alternatively 2–10, z has a value of 2–500, alternatively 2–50, or alternatively 2–10; m has a value of 3–5; n is one; a has a value of 3–6; b has a value of 4–20; c has a value of 0–5; and R3 is hydrogen, a methyl radical, or an acyl radical such as acetyl. Preferably, R1 is methyl; b is 6–12; c is zero; and R3 is hydrogen.

Typically, the long chain or high molecular weight silicone polyether is chosen such that the ratio of x/y or x/z, as described in the structures above, ranges from 2:1 to 50:1, alternatively from 5:1 to 20:1, or alternatively from 10:1 to 12:1.

An cosurfactant can be added as an optional component in this emodiement. When used, the cosurfactant is selected from a monohydroxy alcohol, an organic diol, an organic triol, an organic tetraol, a silicone diol, a silicone triol, a silicone tetraol, and a nonionic organic surfactant. Some representative examples of the optional cosurfactant component (iv) include monohydroxy alcohols such as methanol, ethanol, and 2-propanol; organic diols such as ethylene glycol and propylene glycol; organic triols such as glycerol; organic tetraols such as pentaerythritol and 1,2,3,6-hexane tetraol; and a silicone tetraol such as shown below.

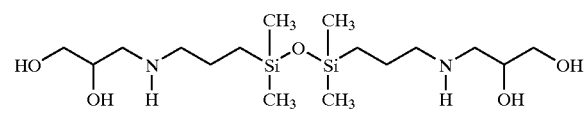

The nonionic surfactant should be a non-silicon atom containing nonionic emulsifier. Most preferred are alcohol ethoxylates $R4-(OCH_2CH_2)_dOH$, most particularly fatty alcohol ethoxylates. Fatty alcohol ethoxylates typically contain the characteristic group—$(OCH_2CH_2)_dOH$ which is attached to fatty hydrocarbon residue R4 which contains about eight to about twenty carbon atoms, such as lauryl ($C_{12}$), cetyl ($C_{16}$) and stearyl ($C_{18}$). While the value of "d" may range from 1 to about 100, its value is typically in the range of 2 to 40. Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under names such as ALFONIC®, ARLACEL, BRIJ, GENAPOL®, LUTENSOL, NEODOL®, RENEX, SOFTANOL, SURFONIC®, TERGITOL®, TRYCOL, and VOLPO.

Compositions according to this embodiment of this invention contain 5–90 percent by weight of total surfactant, i.e. the combination of component (iii), and when used, component (iv). Preferably the compositions according to this embodiment contain 15–50 percent by weight of total surfactant. When cosurfactant is used, the weight ratio of long chain or high molecular weight silicone polyether to cosurfactant should range from 20/80 to 95/5. The balance of the composition is volatile siloxane and water, with the proportions of volatile siloxane and water generally being in the ratios of 5:95 to 95:5, respectively, alternatively 5:95 to 30:70, or alternatively 70:30 to 95:5.

In a second embodiment of the invention, clear microemulsion are formed by simply combining the components (i) water; (ii) a volatile siloxane; (iii) a nonvolatile siloxane; (iv) a silicone polyether; and as an optional component, (v) a cosurfactant such as a monohydroxy alcohol, an organic diol, an organic triol, an organic tetraol, a silicone diol, silicone triol, silicone tetraol, or a nonionic organic surfactants.

The volatile siloxane and optional cosurfactant components used in this second embodiment are the same as described above for the first embodiment.

The silicone polyether can be a long chain or high molecular weight silicone polyether, as described above in the first embodiment, a short chain or low molecular weight silicone polyether, or combinations of both. Short chain or low molecular weight silicone polyether suitable in this second embodiment have a structure represented by:

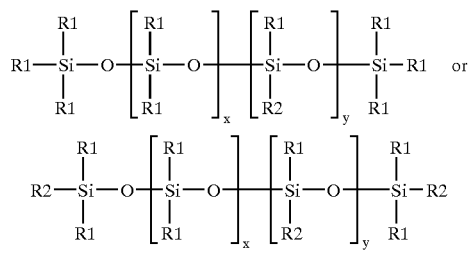

A cyclic polyether of the type shown below can also be used.

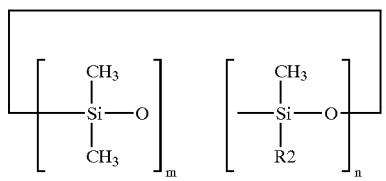

In these structures, R1 represents an alkyl group containing 1–6 carbon atoms such as methyl, ethyl, propyl, butyl, pentyl, and hexyl; R2 represents the radical—$(CH_2)_aO(C_2H_4O)_b(C_3H_6O)_cR3$; x has a value of 0–19, alternatively 1–10, or alternatively 1–5; y has a value of 1–20, or alternatively 1–5, z has a value of 1–20, or alternatively 1–5, with the proviso that x+y or x+z is less than or equal to 21; m has a value of 3–5; n is one; a has a value of 3–6; b has a value of 4–20; c has a value of 0–5; and R3 is hydrogen, a methyl radical, or an acyl radical such as acetyl. Preferably, R1 is methyl; b is 6–12; c is zero; and R3 is hydrogen.

The silicone polyether surfactants can be prepared by any of the techniques known in the art, and many are commercially available. Representative commercial silicone polyether surfactants suitable in the present invention include DC 5329 as the long chain or high molecular weight silicone polyether and DC 5211 as the short chain or low molecular weight polyether (Dow Corning Corporation, Midland, Mich.).

Compositions according to the second embodiment of the invention contain 5–90 percent by weight of total surfactant, as defined above, preferably 15–50 percent by weight. The balance of the composition is the siloxane phase (i.e. the combination of components (ii) and (iii)) and water, in proportions of siloxane phase and water generally in the ratios of 5:95 to 95:5. The nonvolatile silicone oil in the mixed siloxane phase constitutes 1–30 percent of the siloxane component.

Silicone oils suitable for use in making clear silicone microemulsions according to this invention include both volatile and nonvolatile linear and cyclic methyl, higher alkyl, or aryl siloxanes.

The compositions of the second embodiment of the present invention also contain non-volatile siloxanes which include linear and cyclic methyl, higher alkyl, or aryl siloxanes. The nonvolatile linear and cyclic higher alkyl and aryl siloxanes are represented respectively by the formulas $R^a_3SiO(R^a_2SiO)_pSiR^a_3$ and $(R^a_2SiO)_r$. $R^a$ can be an alkyl group with 1–20 carbon atoms, or an aryl group such as phenyl. $R^a$ can also be hydrogen, an aralkyl (arylalkyl) group such as benzyl, or an alkaryl (alkylaryl) group such as tolyl. The value of p is 0–80, preferably 5–20. The value of r is 3–9, preferably 4–6. These polysiloxanes generally have a viscosity in the range of about 5–100 mm²/s.

Nonvolatile polysiloxanes can also be used where p has a value sufficient to provide siloxane polymers with a viscosity in the range of about 100–1,000 mm²/sec. Typically, p can be about 80–375. Illustrative of such polysiloxanes are polydimethylsiloxane, polydiethylsiloxane, polymethylethylsiloxane, polymethylphenylsiloxane, polydiphenylsiloxane, and polymethylhydrogensiloxane.

EXAMPLES

The following examples are set forth in order to illustrate the invention in more detail. In these examples, the symbol M is used to indicate the monofunctional polyorganosiloxane structural unit $R_3SiO_{1/2}$, while the symbol D is used to indicate the difunctional polyorganosiloxane structural unit $R_2SiO_{2/2}$.

Example 1
Preparation of Single Phase Oil and Water Compositions with Polymeric Silicone Surfactants A 60/40, 70/30 and 80/20 mixture of silicone polyether (SPE), and 1,2-hexanediol were each prepared by heating the SPE for 45 seconds in a microwave oven, and then adding 1,2-hexanediol. The mixtures were shaken and spun on the rotary wheel of a Model 7637-01 Roto-Torque device for thirty minutes. The mixtures were all used at room temperature.

For each sample, a triangular graph was used to determine the desired percentages of each of the three components to be used. Using a Mettler AG204 analytical balance, samples with a total mass of three gram were prepared. For example, 1.65 g of surfactant (60/40) was first weighed into a 13×100 mm Pyrex tube vial, 1.215 g of deionized water was added, and finally 0.135 g of volatile siloxane $D_5$. Other samples prepared included (i) 1.5 g of surfactant (70/30), 1.35 g of deionized water, and 0.15 g of $D_5$ fluid; and (ii) 1.5 g of surfactant (80/20), 1.35 g of deionized water, and 0.15 g of $D_5$ fluid. The sample tube vials were each labeled and spun on the rotary wheel for ten minutes. All formed clear microemulsions.

Microemulsions were also formed using an SPE, diethylene glycol monohexyl ether, $D_5$ fluid, and deionized water. The best results were obtained using compositions comprising (i) 1.5 g of the 50/50 surfactant, 0.15 g of $D_5$ fluid, and 1.35 g of water; (ii) 0.6 g of 50/50 surfactant, 0.24 g $D_5$ fluid, and 2.16 g of water; and (ii) 1.8 g of 50/50 surfactant, 0.6 g of $D_5$ fluid, and 0.6 g of water.

TABLE 1

| Percent Surfactant | % H$_2$O | Percent Oil | Appearance |
| --- | --- | --- | --- |
| 55% SPE/1,2-hexanediol (60/40) | 40.50 | 4.5% D$_5$ fluid | Clear |
| 50% SPE/1,2-hexanediol (70/30) | 45 | 5% D$_5$ fluid | Clear |
| 50% SPE/1,2-hexanediol (80/20) | 45 | 5% D$_5$ fluid | Clear |
| 50% SPE/C$_6$E$_2$ (50/50) | 45 | 5% D$_5$ fluid | Clear |
| 20% SPE/C$_6$E$_2$ (50/50) | 72 | 8% D$_5$ fluid | Clear |
| 60% SPE/C$_6$E$_2$ (50/50) | 20 | 20% D$_5$ fluid | Clear |

In this example and in Table 1, SPE represents the long chain or high molecular weight silicone polyether (SPE) with a structure corresponding to $MD_{22}D'(EO_{12})_2M$. $C_6E_2$ represents the nonionic cosurfactant diethylene glycol monohexyl ether. $D_5$ is the volatile siloxane decamethylcyclopentasiloxane.

Examples 2 to 4

Preparation of Single Phase Oil and Water Compositions Using Mixtures Containing Low and High Molecular Weight Silicone Oils In these examples, microemulsions were prepared using the short chain or low molecular weight SPE surfactant $MD'(EO_7)M$, and the other components shown below in Tables 2–4.

TABLE 2

Example 2 - Microemulsions Formed at 39–70° C.

| Component | Actual Weight, gram |
| --- | --- |
| Surfactant, MD'(EO$_7$)M | 1.0498 |
| Oil, Decamethylcyclopentasiloxane | 0.6276 |
| Oil, Polydimethylsiloxane, 10 cs | 0.1558 |
| Water | 1.1704 |

TABLE 3

Example 3 - Microemulsions Formed at 41–75° C.

| Component | Actual Weight, gram |
| --- | --- |
| Surfactant, MD'(EO$_7$)M | 0.9031 |
| Oil, Decamethylcyclopentasiloxane | 0.6293 |
| Oil, Polymethylhydrogensiloxane | 0.2106 |
| Water | 1.2613 |

The polymethylhydrogensiloxane oil used in Example 3 and shown in Table 3 was a nonvolatile siloxane, and consisted of a trimethylsiloxy endblocked dimethyl methylhydrogen siloxane polymer with a viscosity of about 7 centistoke. It had a structure generally represented by $MD_{8.7}D^H_{3.7}M$.

TABLE 4

Example 4 - Microemulsions Formed at 35–45° C.

| Component | Actual Weight, gram |
|---|---|
| Surfactant, MD'(EO$_7$)M | 1.0514 |
| Oil, Decamethylcyclopentasiloxane | 0.7413 |
| Oil, Polydimethylsiloxane, 50 cs | 0.04 |
| Water | 1.1733 |

Example 5
Preparation of Microemulsion with ABA Type SPE

Six gram of a non-crosslinked and long chain or high molecular weight silicone polyether of the formula M'D$_{50}$M' wherein M' represents $(CH_3)_2[(CH_2)_{30}(CH_2CH_2O)_7H]$ SiO— and D is $(CH_3)_2SiO=$; 2.0 gram of the volatile silicone oil D5, i.e. decamethylcyclopentasiloxane, were loaded into a plastic container and mixed with a dental mixer for 20 seconds. Two gram of deionized water was added and mixed with the dental mixer for 20 seconds, resulting in a clear gel.

Example 6
Preparation of Microemulsion with Rake Type SPE 1

5.05 gram of a non-crosslinked and long chain or high molecular weight silicone polyether of the formula MD$_{22}$D'$_2$M wherein M represents $(CH_3)_3SiO—$, D is $(CH_3)_2SiO=$, and D' represents $(CH_3)[(CH_2)_{30}(CH_2CH_2O)_7H]$ SiO=; and 2.83 gram of volatile silicone oil D5, were loaded into a plastic container and mixed with a dental mixer for 20 seconds. 2.11 gram of deionized water was added and mixed with the dental mixer for 20 seconds, resulting in a clear gel.

Example 7
Preparation of Microemulsion with Rake Type SPE 2

4.02 gram of a non-crosslinked and long chain or high molecular weight silicone polyether of the formula MD$_{196.6}$D'$_{63.4}$M wherein M is $(CH_3)_3SiO—$, D is $(CH_3)_2SiO=$, and D' represents $(CH_3)[(CH_2)_{30}(CH_2CH_2O)_7H]$ SiO=, and 2.4 gram of volatile silicone oil D5, were loaded into a plastic container and mixed with a dental mixer for 20 seconds. 3.61 gram of deionized water was added and mixed with the dental mixer for 20 seconds, resulting in a clear gel.

The microemulsions prepared according to the invention can be used in various over-the-counter (OTC) personal care products. Thus, they can be used in antiperspirants, deodorants, skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, color cosmetic removers, and powders. The microemulsion compositions are also useful as carriers for pharmaceuticals, biocides, herbicides, pesticides, and to incorporate water and water-soluble substances into hydrophobic systems.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A microemulsion composition comprising:
   (i) water;
   (ii) a volatile siloxane;
   (iii) a long chain or high molecular weight silicone polyether having the formula

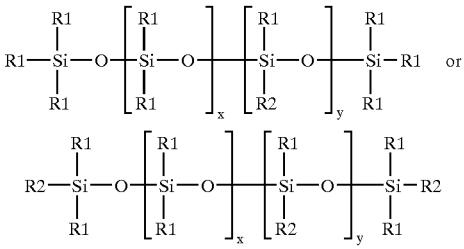

where R1 represents an alkyl group containing 1–6 carbon atoms;
   R2 represents the radical $—(CH_2)_aO(C_2H_4O)_b(C_3H_6O)_cR3$;
   x is 20–1,000; y is 2–500; z is 2–500; a is 3–6; b is 4–20; c is 0–5; and R3 is hydrogen, a methyl radical, or an acyl radical;
   (iv) an optional cosurfactant selected from an organic diol, an organic triol, an organic tetraol, a silicone diol, a silicone triol, a silicone tetraol, and a nonionic organic surfactant;
   (v) a non-volatile siloxane; wherein the microemulsion contains 5–90 percent by weight of components (iii) and (iv), the balance of the microemulsion comprising the siloxane phase and the water in a ratio of 5:95 to 95:5 respectively, with the non-volatile siloxane comprising 1–30 percent by weight of the total amount of the volatile siloxane and the non-volatile siloxane.

2. A microemulsion composition according to claim 1 in which the cosurfactant is present and is an organic diol.

3. A microemulsion composition according to claim 2 in which the organic diol is 1,2-hexanediol or diethylene glycol monohexyl ether.

4. A microemulsion composition according to claim 1 in which the volatile siloxane (ii) is a volatile linear methyl siloxane of the formula $(CH_3)_3SiO\{(CH_3)_2SiO\}_kSi(CH_3)_3$ where k is 0–5; or a cyclic methyl siloxane of the formula $\{(CH_3)_2SiO\}_t$ where t is 3–9; the volatile siloxane having a boiling point less than about 250° C., and a viscosity of 0.65–5.0 mm$^2$/s.

5. A microemulsion composition according to claim 1 in which non-volatile siloxane (v) is a nonvolatile linear or cyclic higher alkyl or aryl siloxane of the formula $R^a_3SiO(R^a_2SiO)_pSiR^a_3$ or $(R^a_2SiO)_r$ where $R^a$ is an alkyl group with 1–20 carbon atoms or an aryl group, hydrogen, an aralkyl (arylalkyl) group, or an alkaryl (alkylaryl) group; p is 0–375; r is 3–9; and the non-volatile siloxane has a viscosity greater than five mm$^2$/s to 1,000 mm$^2$/sec.

\* \* \* \* \*